United States Patent [19]

Yamamoto et al.

[11] Patent Number: 5,635,486
[45] Date of Patent: Jun. 3, 1997

[54] OPHTHALMIC COMPOSITION COMPRISING A SLEEP ADJUSTING SUBSTANCE

[75] Inventors: Kozo Yamamoto, Takasago; Takayoshi Hidaka, Kobe, both of Japan

[73] Assignee: Kanegafuchi Kagaku Kogyo Kabushiki Kaisha, Osaka, Japan

[21] Appl. No.: 302,236

[22] Filed: Sep. 7, 1994

Related U.S. Application Data

[63] Continuation of Ser. No. 993,421, Dec. 21, 1992, abandoned.

[30] Foreign Application Priority Data

May 11, 1990 [JP] Japan ................................ 2-121786

[51] Int. Cl.$^6$ .......................... A61K 31/70; A61K 31/495
[52] U.S. Cl. ........................... 514/32; 514/255; 514/912
[58] Field of Search ........................... 514/32, 255, 912

[56] References Cited

PUBLICATIONS

H. Nishino, Zoku Baiorizumu to Sono Kiko, Kodansha Scientic, 1978, pp. 203–214, "Amatomical and Functional Communication Between Suprachiasmatic Nucleus and Other Center Sites".

A.A. Borbely et al, Physiological Reviews, vol. 69, No. 2, Apr. 1989, pp. 605–657, "Endogenous Sleep Promoting Substances and Sleep Reguration".

Arendt et al, British Medical Journal, vol. 292, p. 1170, May 1986, "Short Reports—Alleviation of Jet Lag by Melatonin: Preliminary Results of Controlled Double Blind Trial".

T. Miyata et al, Life Sciences, vol. 15, pp. 1135–1152, 1974, "Effects of Inbacerebral Administration of Piperidine on EEG and Behavior".

Y. Komoda et al, Chem. Pharm. Bull., 38(7) pp. 2057–2059, Jul. 1990, "SPS B, A Physiological Sleep Regulator, From the Brainstems of Sleep–Deprived Rats, Identified as Oxidized Glutathione".

G.A. Schoenenberger et al, Proc. Natl. Acad. Sci. USA, vol. 74, No. 3, pp. 1282–1286, Mar. 1977, "Characterization of a delta–electroence–phalogram(–sleep)–inducing peptide".

D. Schneider–Helmert et al, Experientia, vol. 37, pp. 913–917, "The Influence of Synthetic DSIP (delta–sleep–including–peptide) on disturbed human sleep". (1981).

K. Honda et al, Report of the Institute for Medical & Dental Engineering, vol. 18, pp. 93–95, 1984, "Little Sleep–Promoting Effects of Intra–ventricularly Infused Uracil in Unrestrained Rats".

H. Matsumura et al, Brain Research, pp. 1–8, 1987, "Awaking Effect of PGE$_2$ Microinjected Into the Preoptic Area of Rats".

S. Inoue et al, Proc. Natl. Acad. Sci. USA, vol. 81, pp. 6240–6244, Oct. 1984, "Differential Sleep–Promoting Effects of Five Sleep Substances Nocturnally Infused in Unrestrained Rats".

J.M. Krueger et al, Am. J. Physiol., 246: R994–999, "Sleep Promoting Effects of Endogenous Pyrogen (Interleukin–1)".

R. Ueno et al, Advances in Prostaglandin, Thromboxane, and Leuko–triene Research, vol. 15, 1985, "Prostaglandin D$_2$: A Cerebral Sleep–Regulating Substance in Rats".

Y. Takahashi et al, Shinkei–Seishin–Yakuri (Japanese Phonetic), vol. 6, No. 4, pp. 235–239, "Toward Clinical Application of Endogenous Sleep–Promoting Factor", 1985.

K. Honda et al, Neuroscience Research, 1, (1984), pp. 243–252, "Uridine as an Active Component of Sleep–Promoting Substance; its Effects of Nocturnal Sleep in Rats".

O. Hayaishi, The Journal of Biological Chemistry, vol. 263, No. 29, Oct. 15, 1988, pp. 14593–14596, "Sleep–Wake Regulation by Prostaglandins D$_2$ and E$_2$".

M. Radulovacki et al, Phychopharmacology (1985) 87, pp. 136–140, "A Comparison of the Dose Response Effects of Pyrimidine Ribonucleosides and Adenosine on Sleep in Rats".

Primary Examiner—Zohreh Fay
Attorney, Agent, or Firm—Renner, Otto, Boisselle & Sklar

[57] ABSTRACT

The present invention provides an ophthalmic composition comprising a sleep inducing substance or a sleep inhibiting substance, and the sleep inducing substance or the sleep inhibiting substance is derived from an organism. Thus, the invention provides an ophthalmic composition comprising a sleep adjusting substance which normalizes irregularity of the rhythm of sleep and a liquid ophthalmic medicament comprising the composition, the composition and the medicament being safe and obtainable by anyone, and a method for regulating the rhythm of sleep comprising instilling the ophthalmic medicament including the sleep adjusting substance to an individual.

8 Claims, 3 Drawing Sheets

● — SALINE
-■- CYTIDINE (100 μM)

● — SALINE
-■- DSIP (100 μM)

● SALINE
■ PIPERIDINE (100μM)

● SALINE
■ GSSG (100μM)

OPHTHALMIC COMPOSITION COMPRISING A SLEEP ADJUSTING SUBSTANCE

This is a continuation application Ser. No. 07/993,421 filed on Dec. 21, 1992, now abandoned.

BACKGROUND OF THE INVENTION

1. Field of the Invention

The present invention relates to an ophthalmic composition comprising a substance for regulating the rhythm of sleep, and a method for regulating the rhythm of sleep by the instillation of a medicament comprising the composition to the eye.

2. Description of the Related Art

Synthetic sleeping drugs have been used to correct the disorder in the rhythm of sleep. A synthetic sleeping drug is administered, if necessary, for example, to those suffered from a so-called jet lag after an overseas trip, a deteriorated physical condition due to three-shift work, nycterine poriomania due to senile dementia, and insomnia due to stress. However, since an excessive dose of some of the synthetic sleeping drugs can cause the death of a taker, close attention must be paid to their administration.

Such synthetic sleeping drugs are divided into two types: a barbiturate type and a non-barbiturate type. The barbiturate type sleeping drugs have a strong effect and thus are highly dangerous. The non-barbiturate type sleeping drugs have relatively moderate effects.

Among such non-barbiturate type sleeping drugs, benzodiazepine type sleeping drugs such as Halcion (trade name) are regarded to be comparatively safe and are widely utilized clinically these days. But it is known that these drugs can cause anterograde amnesia. It is unknown how the amnesia occurs, but the cause is presumed to be as follows. Sleep is generally divided into two types on the basis of the characteristics thereof: Non-REM sleep (slow wave sleep) and REM sleep (paradoxical sleep). The physiological meanings of the two types have not been fully understood as yet, but it is known that a rat that has been experimentally deprived of REM sleep, that is, a REM sleep deprivation rat, suffers from memory defect for a long period of time. Therefore, REM sleep is definitely concerned with memory fixing. The benzodiazepine type sleeping drugs lower the function of the brain and shorten the duration of REM sleep, and so they can induce anterograde amnesia. Therefore, such benzodiazepine type sleeping drugs are not suitable for patients with senile dementia who can easily fall into amnesia or other defects of memory and for students preparing themselves for an examination who should maintain their memory as clearly as possible.

Since the synthetic sleeping drugs are somewhat dangerous in this manner, it is impossible to obtain them without the prescription of a doctor, which causes inconvenience for those who are not under medical treatment.

On the other hand, sleep inducing substances derived from an organism have been reported as being different from the above described synthetic sleeping drugs. Substances derived from an organism herein mean substances existing in a body of an organism. Examples of such substances include those synthesized in the body of an organism and those from outside a body and utilized after intake for metabolism. It is known that these sleep inducing substances induce natural and physiological sleep without reducing the hours of REM sleep (Borbely et al., *Physiol. Rev.*, 69: 605 (1989)). Such substances do not cause anterograde amnesia as the synthetic sleeping drugs do. Sleep inhibiting substances derived from an organism are also known, and there is no report of any habituation by using such sleep inhibiting substances over a long period of time.

Therefore, these sleep inducing substances and sleep inhibiting substances both derived from organisms (hereinafter referred to as the "sleep adjusting substances") are very useful in treating any disorder in the rhythm of sleep.

As an administration method of a sleeping drug, an oral administration or an injection is generally used, and the oral administration is preferred because it is simple. However, the sleep inducing or sleep inhibiting substances derived from organisms is significantly effective only when they are administered directly into a cerebral ventricle. There are a few reports that it was effective to administer them into an abdominal cavity. But the administration into the cerebral ventricle or abdominal cavity is neither convenient nor practical. As the oral administration of these substances, relief of jet lag by orally administering melatonin has been reported (Arendt et al., *Br. Med. J.*, 292: 1170 (1986); and oral administration of tryptophan is known. In these cases, the oral administration is somewhat effective, but there is no report, except for the above, that the oral administration of the above described sleep adjusting substances derived from an organism is effective. This is because these substances have a disadvantage that they are easily metabolized in an organism and scarcely reach the region for adjusting the biological rhythm in the brain since they are derived from an organism. Therefore, it has been impossible to put these substances to practical use.

SUMMARY OF THE INVENTION

The ophthalmic composition of the invention comprises at least one sleep adjusting substance.

In one aspect of the invention, the sleep adjusting substance is derived from an organism.

In another aspect of the invention, the sleep adjusting substance derived from an organism is at least one sleep inducing substance selected from the group consisting of uridine, sleep promoting substance, adenosine, prostaglandin $D_2$, delta-sleep-inducing peptide, piperidine, 2-octyl-gamma-bromoacetoacetate, arginine vasotocin, melatonin, serotonin, tryptophan, oxidized glutathione, and derivatives thereof.

In another aspect of the invention, the sleep adjusting substance derived from an organism is at least one sleep inhibiting substance selected from the group consisting of cytidine, prostaglandin $E_2$, delta-sleep-inducing peptide, and derivatives thereof.

Thus, the invention described herein makes possible the advantages of (1) providing an ophthalmic composition comprising a sleep adjusting substance which normalizes irregularity of the rhythm of sleep and a liquid ophthalmic medicament comprising the composition, the composition and the medicament being safe and obtainable by anyone, and (2) providing a method for regulating the rhythm of sleep comprising instilling the ophthalmic medicament including the sleep adjusting substance to an individual.

These and other advantages of the present invention will become apparent to those skilled in the art upon reading and understanding the following de- tailed description with reference to the accompanying figures.

DESCRIPTION OF THE PREFERRED EMBODIMENTS

Figure 1:
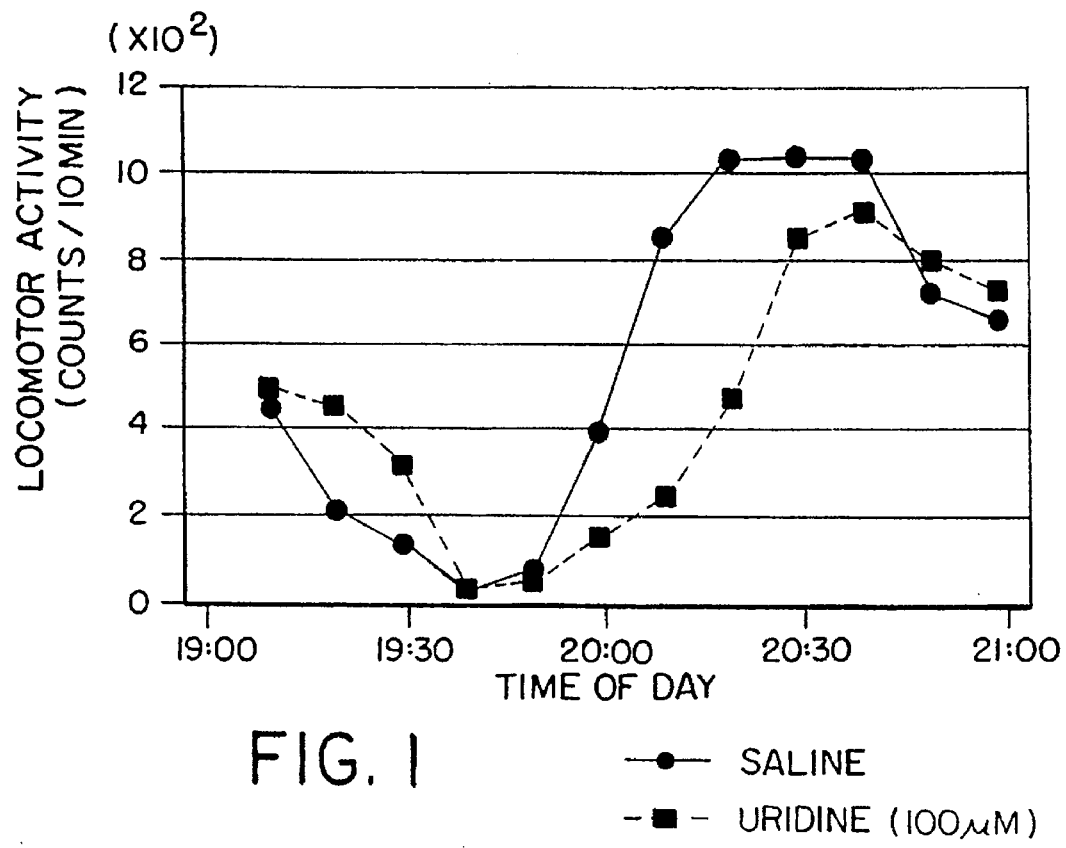
FIG. 1 is a graph showing a change with time in the locomotor activity of a mouse which is instilled with an ophthalmic medicament prepared from an ophthalmic composition of the present invention including uridine.

Examples of the sleep inducing substances derived from an organism used in the present invention include uridine, sleep promoting substance (SPS), adenosine, prostaglandin $D_2$ ($PGD_2$), delta-sleep-inducing peptide (DSIP), piperidine, 2-octyl-gamma-bromoacetoacetate (gammabrom), arginine vasotocin (AVT), melatonin, serotonin, tryptophan and oxidized glutathione (GSSG).

Among the above-mentioned substances, SPS is a sleep inducing substance derived from a sleep deprivation mouse. The structure thereof is now being elucidated. Uridine is a part of an SPS molecule. It has been reported that an injection of only 10 pmole of uridine into a cerebral ventricle induces non-REM sleep (Honda et al., Neurosci. Res., 1: 243 (1984)). Therefore, uridine is most appropriate in cases such as in the present invention where a small amount of the substance is expected to be transported into a brain by the instillation to the eye. Adenosine, which is relative to uridine, is also known to induce non-REM sleep by being administered into a lateral venticle of a rat. $PGD_2$ is a strong sleep inducing substance discovered by Hayaishi et al., and contrasts with $PGE_2$ which is also included in the prostaglandins but inhibits sleep (Osamu Hayaishi, J. Biol. Chem., 263: 14593 (1988)). Piperidine is one of the endogenous amines existing in the brains of mammals and is known to exhibit a sleep inducing activity (Miyata et al., Life Sci., 15: 1135 (1974)). Moreover, piperidine is suggested to play an important role in hibernation. 2-Octyl-gamma-bromoacetoacetate, which is commonly called gammabrom, is a REM sleep inducing substance extracted from human cerebrospinal fluid. Melatonin and AVT are pineal body hormones, the former is considered to adjust the biological rhythm, while the latter induces non-REM sleep in an animal and REM sleep in a human by increasing the amount of serotonin in the brain. Serotonin is a neurotransmitter that has been suggested to be concerned in sleep for a long time, and tryptophan is a precursor of serotonin. Oxidized glutathione (GSSG) was revealed by Komoda Y. et al. (Chem. Pharm. Bul., 38: 2057 (1990)) as an essence of SPS-B, a part of an SPS molecule as is uridine. Even a small amount of oxidized glutathione injected into a brain lengthens both non-REM sleep hours and REM sleep hours.

Examples of the sleep inhibiting substances derived from an organism used in the present invention include cytidine, prostaglandin $E_2$ and DSIP. Among these sleep inhibiting substances, cytidine has been reported to increase arousal hours and decrease total sleep hours when administered into a cerebral ventricle (Radulovacki et el., Psychopharmacology, 87: 136 (1985)). The sleep inhibiting activity of prostaglandin $E_2$ was found by Matsumura, a member of the Hayaishi group. DSIP is a peptide comprising nine amino acids, end is known to induce sleep when administered into a cerebral ventricle of a rabbit (Schoenenberger et el., Proc. Natl. Aced. Sci USA, 74: 1282 (1977)). DSIP is also known to have an anti-stress activity such as causing sleep inhibition when administered to a human (Schneider-Helmert et el., Experientia, 37: 913 (1981)).

Such sleep adjusting substances can be obtained by isolating and purifying the substance from an organism; by producing with a genetic engineering technique; or by chemical synthesizing.

The ophthalmic composition of the present invention can be obtained by combining the sleep adjusting substance with, if necessary, additives generally used in an ophthalmic medicament such as an isotonic agent, a buffer, and a preservative; and additives for enhancing the function of the used sleep adjusting substance. An example of the isotonic agent includes sodium chloride. Examples of the buffer include boric acid, sodium hydrogenphosphate and disodium hydrogenphosphate. Examples of the preservative include benzalkonium chloride, benzethonium chloride and chlorobutanol. Examples of the additives for enhancing the activity include a degrading enzyme inhibitor and a viscosity improver. The amount of each additive depends upon the kind of the used sleep adjusting substance and the additive. Moreover, the ophthalmic composition can contain the sleep adjusting substance alone or in combination with an additive except for the above.

The ophthalmic medicament comprising sleep adjusting substances derived from an organism is prepared by dissolving the ophthalmic composition of the present invention in sterilized purified water or saline; or dissolving the ophthalmic composition of the present invention in water or saline, followed by sterilization. The above-mentioned additives can be added at the time of dissolving the ophthalmic composition comprising the sleep adjusting substance alone in water or saline. The sleep adjusting substance derived from an organism is contained in such an ophthalmic medicament generally at a concentration of 1 µM to 1 nM, preferably 10 µM to 100 µM.

When the ophthalmic medicament of the present invention is instilled, the sleep adjusting substance contained in the ophthalmic medicament is uptaken by ganglion cells in the retina. The uptaken substance is transported to a suprachiasmatic nucleus in the brain via a transporting system in the neuron called an axonal flow of a neural projection designated as a retino-hypothalamic tract. The suprachiasmatic nucleus is a part of the hypothalamus and is just above the optic chiasma. Especially in a mammal, the suprachiasmatic nucleus is regarded as a site where a biological clock exists. It is generally known that a functional site of a sleep promoting substance is somewhere between the hypothalamus and the lower part of the thalamus. Therefore, the suprachiasmatic nucleus, which is a part of the hypothalamus, is considered to be concerned in the rhythm of sleep, which is an important element of one's circadian rhythm. Accordingly, the administered sleep adjusting substance works at this point, resulting in adjusting the sleep-wake rhythm through its center.

Moore et al. (J. Comp. Nuer., 146: 1 (1972)) have reported on the retino-hypothalamic tract existing between the retina of an eyeball and the suprachiasmatic nucleus. According to a report by H. Nishino, when horseradish peroxidase, an enzyme with a molecular weight of about 40,000, which is frequently used as a tracer due to its histochemical dyeing ability, injected into an eyeball, it is uptaken by the ganglion cells, and then transported to the suprachiasmatic nucleus through the axonal flow (Zoku Baiorizumu to Sono Kiko (Japanese phonetics), Kodansha Scientific, 1978, pp. 203-214).

When the ophthalmic medicament comprising the ophthalmic composition of the present invention is administered, in order to exhibit its activity the sleep adjusting substance contained therein can be transported to the suprachiasmatic nucleus through other nerve conduction paths, or can directly affect neurons of the retina and the like. For example, it has been reported that uridine induces or inhibits excitation of the neurons, and can affect the nervous system distributed in the retina and the eyeball.

EXAMPLES

The present invention will now be illustrated by the following examples.

(Test method)

Three ICR male mice were put in a cage and bred under the condition of a day-and-night cycle of every 12 hours (the daytime: from 7:35 to 19:35; the nighttime: from 19:35 to 7:35) for an experiment. Since the mice are nocturnal, they remain inactive until several tens minutes after the lights-out. When saline was administered to the mice by the instillation to the eye 30 minutes before the lights-out, the locomotor activity of the mice was temporarily increased. However, the activity faded within 30 minutes after the instillation and then disappeared. The group that had the saline instillation became active about 30 minutes later than the group without the saline instillation. Namely, the mice with the saline instillation became active about 20:10, which is about 1 hour after the administration of the saline.

In this manner, the mice were habituated to the instillation by administering the saline every day. After the same activity pattern appeared for two days continuously, an ophthalmic medicament containing a desired sleep adjusting substance was instilled for consecutive two days. The ophthalmic medicament was prepared by dissolving the sleep adjusting substance in saline. Thirty five minutes before the lights-out (at 19:00), about 5 μl of the ophthalmic medicament comprising the sleep adjusting substance (100 μM) was instilled into each eye of the mouse, respectively. The locomotor activity (unit: count) of mice was measured every 10 minutes by using a measuring device for the locomotor activity of an experimental animal "Automex" (produced by Tokai Irika). The locomotor activity was measured by putting a mouse on the measuring device. Every time any of the mice moved, a counter of the device cumulated the number of the movements. Thus, the larger cumulated number reflected more energetic activity. Such a measurement was conducted twice (for two days). An average value of the locomotor activity at each time was calculated and the results were plotted to obtain a graph, with time as the abscissas and the average locomotor activity as the ordinates. This graph depicts an activity pattern of the mice as a function of an administration of the ophthalmic medicament. A total of the locomotor activity (i.e., an area below the curve in the graph) per one hour between 19:30 which is 30 minutes after the administration and 20:30 was calculated. In the same manner, as for the mice with the administration of saline alone, a total locomotor activity per the same one hour period as above was calculated. The ratio (%) of the calculated total locomotor activity per one hour of the mice with saline alone to that of the mice with the administration of the ophthalmic medicament (hereinafter called the "total activity ratio") was obtained. The mice whose activity patterns were not stable during the habituation to the administration of saline were not used in the following examples.

Example 1

[A sleep inducing activity by uridine]

Uridine was used as the sleep adjusting substance derived from an organism. The total activity ratio (%) is shown in Table 1, and the activity pattern of the mice with the instillation of the ophthalmic medicament containing 100 μM of uridine is shown in FIG. 1. As is apparent from FIG. 1 and Table 1, the time when the mice started to move shifted backward in the group with the administration of uridine and the locomotor activity thereof was remarkably decreased.

Inoue et al. has reported that uracil, a component of uridine, does not have a sleep inducing activity (Honda et al., Reports Med. Dent. Eng., 18: 93 (1984)). When an ophthalmic medicament including 100 μM of uracil was instilled to a mouse, the locomotor activity of the mouse did not decrease (Table 1). Thus, the ophthalmic medicament including uridine showed a sleep inducing activity by the instillation.

Next, an ophthalmic medicament including 100 μM of uridine was instilled to the ICR mice continuously for 2 weeks. There was no change in the weight gain of the mice as compared with the group without the instillation of uridine, and any change of an eyeball and/or internal organs was not visually observed.

TABLE 1

| Change of the locomotor activity by uridine | | |
|---|---|---|
| Compound | Concentration (μM) | Total Activity ratio per hour (% of control) |
| Uridine | 10 | 63 |
| Uridine | 30 | 57 |
| Uridine | 100 | 53 |
| Uracil | 100 | 110 |

Example 2

[A sleep inducing activity by prostaglandin $D_2$ ($PGD_2$)]

Figure 2:
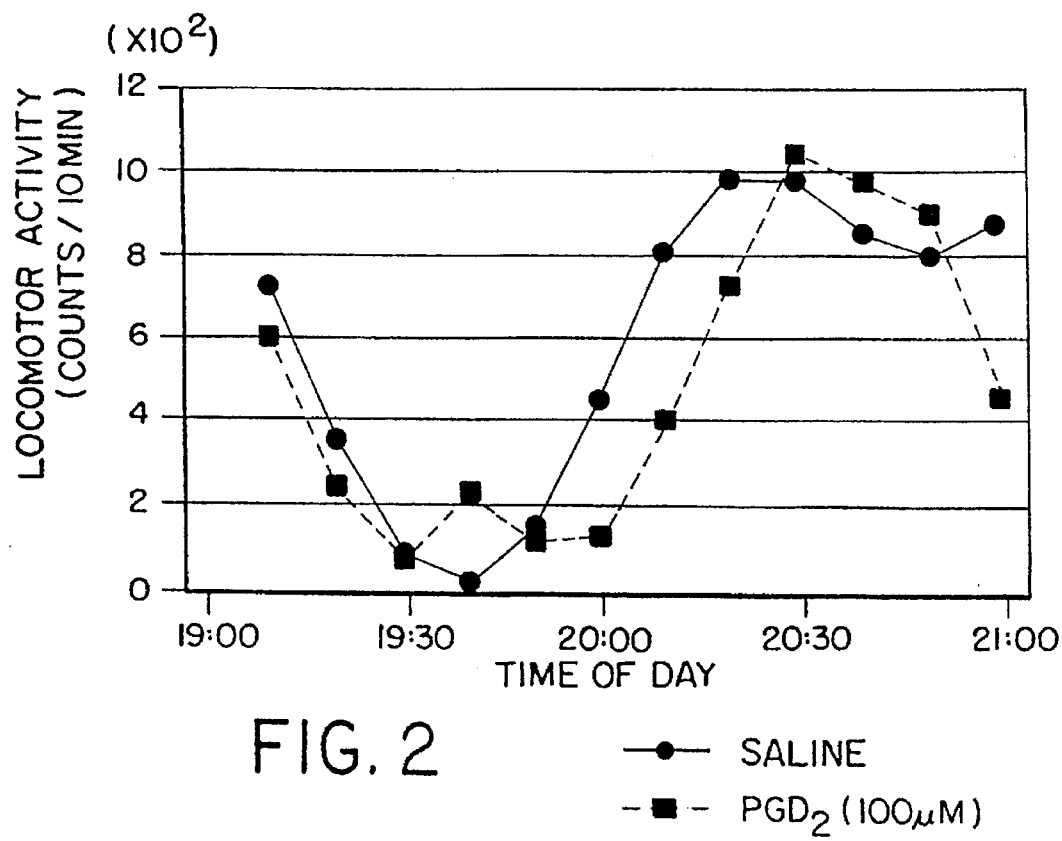
FIG. 2 is a graph showing a change with time in the locomotor activity of a mouse which is instilled with an ophthalmic medicament prepared from an ophthalmic composition of the present invention including prostaglandin $D_2$ ($PGD_2$).

$PGD_2$ was used as the sleep adjusting substance. As is shown in FIG. 2, the time when the mice started to move shifted backward by the instillation of an ophthalmic medicament including 100 μM of $PGD_2$. The total activity ratio was reduced to 78% of the control group.

Example 3

[A sleep inhibiting activity by cytidine]

Figure 3:
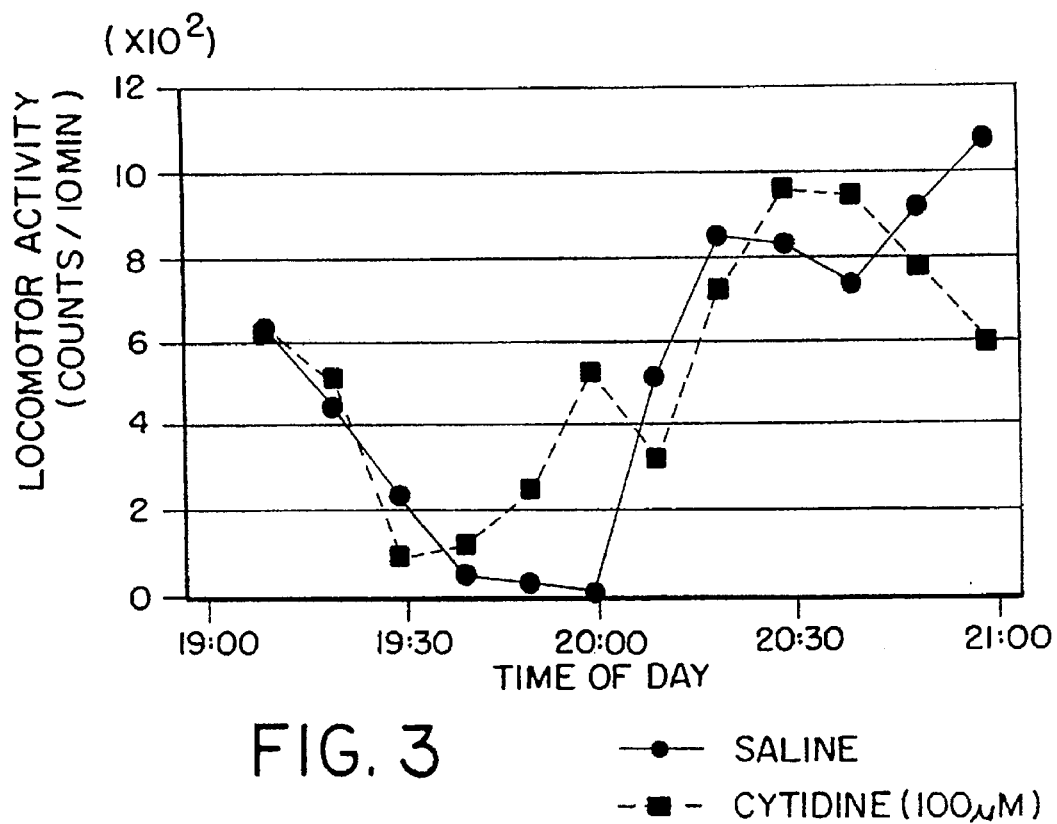
FIG. 3 is a graph showing a change with time in the locomotor activity of a mouse which is dosed with an ophthalmic medicament prepared from an ophthalmic composition of the present invention including cytidine.

Cytidine was used as the sleep adjusting substance. The time when the mice started to move advanced by the instillation of an ophthalmic medicament including 100 μM of cytidine, and the total activity ratio rose to 127% (FIG. 3).

This suggests that the instillation of cytidine can inhibit sleep. This sleep inhibition is not caused by a pain or an itch in the eyes, supported by the fact that the locomotor activity completely disappeared temporarily after the instillation. Thus, there is a time lag between the installation of the sleep adjusting substance and the activity affected thereby, which is considered to be due to the time required to transport the substance through the axonal flow.

Example 4

[A sleep inhibiting activity by DSIP]

Figure 4:
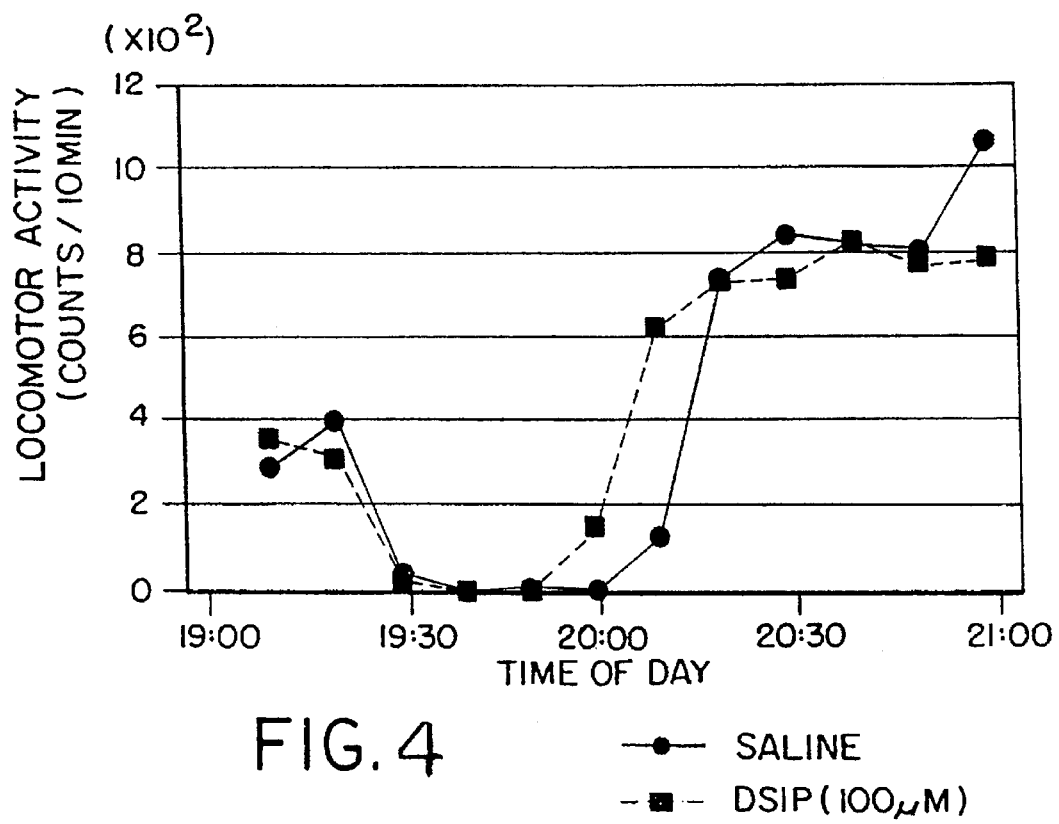
FIG. 4 is a graph showing a change with time in the locomotor activity of a mouse which is dosed with an ophthalmic medicament prepared from an ophthalmic composition of the present invention including delta-sleep-inducing peptide (DSIP).

DSIP was used as the sleep adjusting substance. DSIP (100 μM) was dissolved in saline containing 0.1% bovine serum albumin. The instillation of the resultant solution exerted a sleep inhibiting activity when measured in the same manner as in the above examples (FIG. 4), and the total activity ratio rose to 130%. This is regarded to show that an instillation, which is stressful for a mouse, was relieved by DSIP. The sleep inhibition is certainly not due to any pain or itch in the eyes for the same reason as was shown in Example 3 using cytidine.

Example 5

[A sleep inducing activity by piperidine]

Figure 5:
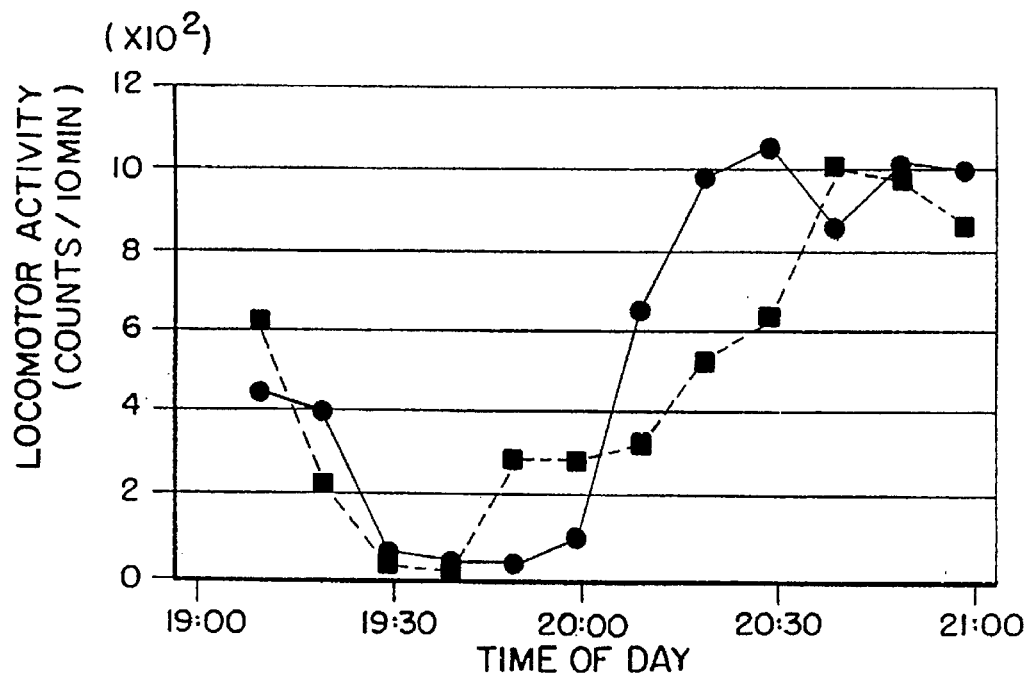
FIG. 5 is a graph showing a change with time in the locomotor activity of a mouse which is dosed with an ophthalmic medicament prepared from an ophthalmic composition of the present invention including piperidine.
Figure 6:
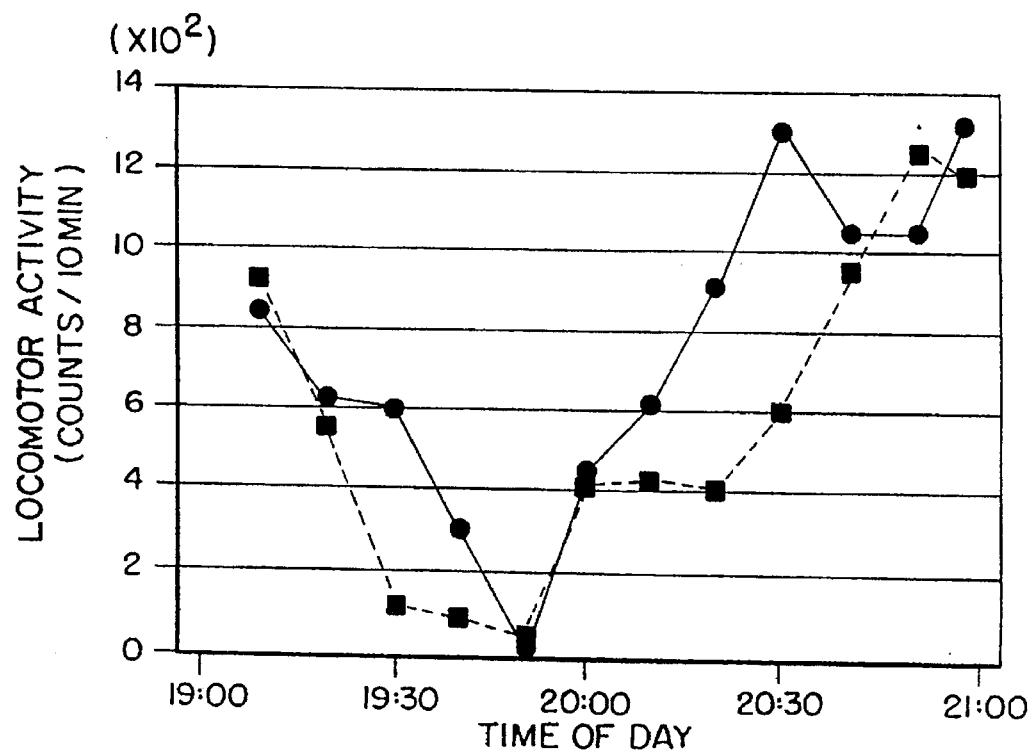
FIG. 6 is a graph showing a change with time in the locomotor activity of a mouse which is dosed with an ophthalmic medicament prepared from an ophthalmic composition of the present invention includ- ing oxidized glutathione (GSSG).

Piperidine (100 μM) was used as the sleep adjusting substance. The activity pattern is shown in FIG. 5, and the total activity ratio per hour was reduced to 72%.

Example 6

[A sleep inducing activity by GSSG]

GSSG (100 μM) was used as the sleep adjusting substance. The activity pattern is shown in FIG. 5, and the total activity ratio per hour was reduced to 72%.

As described above, the ophthalmic composition comprising the sleep inducing substance or the sleep inhibiting substance both derived from an organism is provided by the present invention. It is possible to allow the sleep adjusting substance, which does not sufficiently exhibit its activity by the conventional oral administration and the like, to affect directly the center by the instillation of the ophthalmic medicament prepared from the ophthalmic composition comprising the sleep adjusting substance. Thus, it is possible to administer a safe sleep adjusting substance in a simple and inexpensive manner.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for regulating a rhythm of sleep comprising administering a sleep adjusting substance into eyes, wherein the sleep adjusting substance is at least one selected from the group consisting of uridine, cytidine, and derivatives thereof.

2. A method according to claim 1, wherein the sleep adjusting substance is at least one selected from the group consisting of uridine and derivatives thereof.

3. A method according to claim 1, wherein the sleep adjusting substance is at least one selected from the group consisting of cytidine and derivatives thereof.

4. A method for regulating a rhythm of sleep comprising administering an ophthalmic composition into eyes, wherein the ophthalmic composition comprises at least one of a sleep adjusting substance selected from the group consisting of uridine, cytidine, and derivatives thereof.

5. A method for regulating a rhythm of sleep comprising administering an ophthalmic medicament into eyes, wherein the ophthalmic medicament comprises an ophthalmic composition which contains at least one of a sleep adjusting substance selected from the group consisting of uridine, cytidine, and derivatives thereof.

6. A method according to claim 5, wherein the ophthalmic medicament is administered by instillation into eyes.

7. A method according to claim 5, wherein the sleep adjusting substance is contained in the ophthalmic medicament at a concentration of 1 μM to 1 mM.

8. A method according to claim 5, wherein the sleep adjusting substance is contained in the ophthalmic medicament at a concentration of 10 μM to 100 μM.

* * * * *